(12) United States Patent
Hodges et al.

(10) Patent No.: US 9,012,705 B2
(45) Date of Patent: Apr. 21, 2015

(54) PROCESS FOR THE PREPARATION OF DICHLOROFULVENE

(75) Inventors: George Robert Hodges, Bracknell (GB); Dominik Faber, Munchwilen (CH); Alan James Robinson, Munchwilen (CH); Andrew Charles Shaw, Sunbury on Thames (GB)

(73) Assignees: Syngenta Paticipations AG, Basel (CH); Syngenta Limited, Guildford, Surrey (GB)

( * ) Notice: Subject to any disclaimer, the term of this patent is extended or adjusted under 35 U.S.C. 154(b) by 229 days.

(21) Appl. No.: 13/818,899

(22) PCT Filed: Aug. 22, 2011

(86) PCT No.: PCT/EP2011/064381
§ 371 (c)(1),
(2), (4) Date: Jul. 12, 2013

(87) PCT Pub. No.: WO2012/025489
PCT Pub. Date: Mar. 1, 2012

(65) Prior Publication Data
US 2013/0281744 A1    Oct. 24, 2013

(30) Foreign Application Priority Data
Aug. 25, 2010    (EP) .................................... 10173992

(51) Int. Cl.
C07C 17/25    (2006.01)
C07C 22/02    (2006.01)
C07C 23/08    (2006.01)

(52) U.S. Cl.
CPC .................. C07C 17/25 (2013.01); C07C 23/08 (2013.01); C07C 2101/10 (2013.01)

(58) Field of Classification Search
CPC .................. C07C 17/25; C07C 22/02

USPC ................................................... 570/226, 186
See application file for complete search history.

(56) References Cited

U.S. PATENT DOCUMENTS 2,721,160  A    10/1955    Newcomer

FOREIGN PATENT DOCUMENTS

WO    2010/049228 A1    5/2010

OTHER PUBLICATIONS

Krebs, Juerg et al: "Fulvenes and fuvalenes. 29. 6-Halofulvenes from lithium carbenoids and cyclopentenone", Chimia, Schweizerische Chemische Gesellschaft, CH, vol. 35, No. 2, Jan. 1, 1981, pp. 55-57.

Primary Examiner — Jafar Parsa
Assistant Examiner — Medhanit Bahta
(74) Attorney, Agent, or Firm — R. Kody Jones

(57) ABSTRACT

The invention relates to a process for the preparation of formula (I) which process comprises pyrolyzing a compound of formula (II) wherein X is chloro or bromo, and to compounds which may be used as intermediates for the manufacture of the compound of formula I and to the preparation of said intermediates.

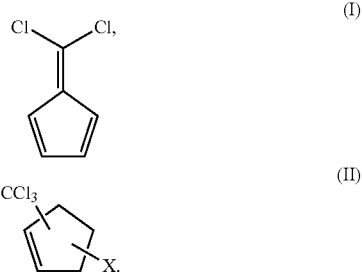

13 Claims, 3 Drawing Sheets

CTCM-CP: compound of formula IId

PROCESS FOR THE PREPARATION OF DICHLOROFULVENE

This application is a 371 of International Application No. PCT/EP2011/064381 filed Aug. 22, 2011, which claims priority to EP 10173992.8 filed Aug. 25, 2010, the contents of which are incorporated herein by reference.

The present invention relates to a process for the preparation of dichlorofulvene from a substituted cyclopentadiene and to compounds which may be used as intermediates for the manufacture of dichlorofulvene and to the preparation of said intermediates.

Dichlorofulvene is an important intermediate for the preparation of fungicidally active carboxamides as described, for example, in WO 2007/048556.

According to WO 2010/049228, dichlorofulvene can be prepared by reacting a compound of formula II

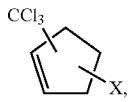
(II)

wherein X is chloro or bromo, with a base like alkali metal alcoholate, for example sodium tert-butoxide or potassium tert-butoxide or a metal amide like NaNH$_2$ or lithiumdiisopropylamide in an appropriate solvent to dichlorofulvene of formula I

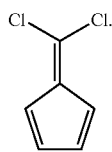
(I)

However, the prior art process has several disadvantages. The obligatory use of more than 2 equivalents of an expensive base makes the process uneconomical. Further, the use of organic solvents and for good yields also catalysts and solubiliser especially for the alkali metal alcoholate bases requires complete separation of said chemicals after the reaction to avoid environmental issues. The isolation of the solvent from the effluent and its water free recycling is cumbersome and technologically difficult.

The aim of the present invention is therefore to provide a novel process for the production of dichlorofulvene that avoids the disadvantages of the known process and makes it possible to prepare dichlorofulvene in high yields and good quality in an economically and ecologically advantageous way.

Figure 1:
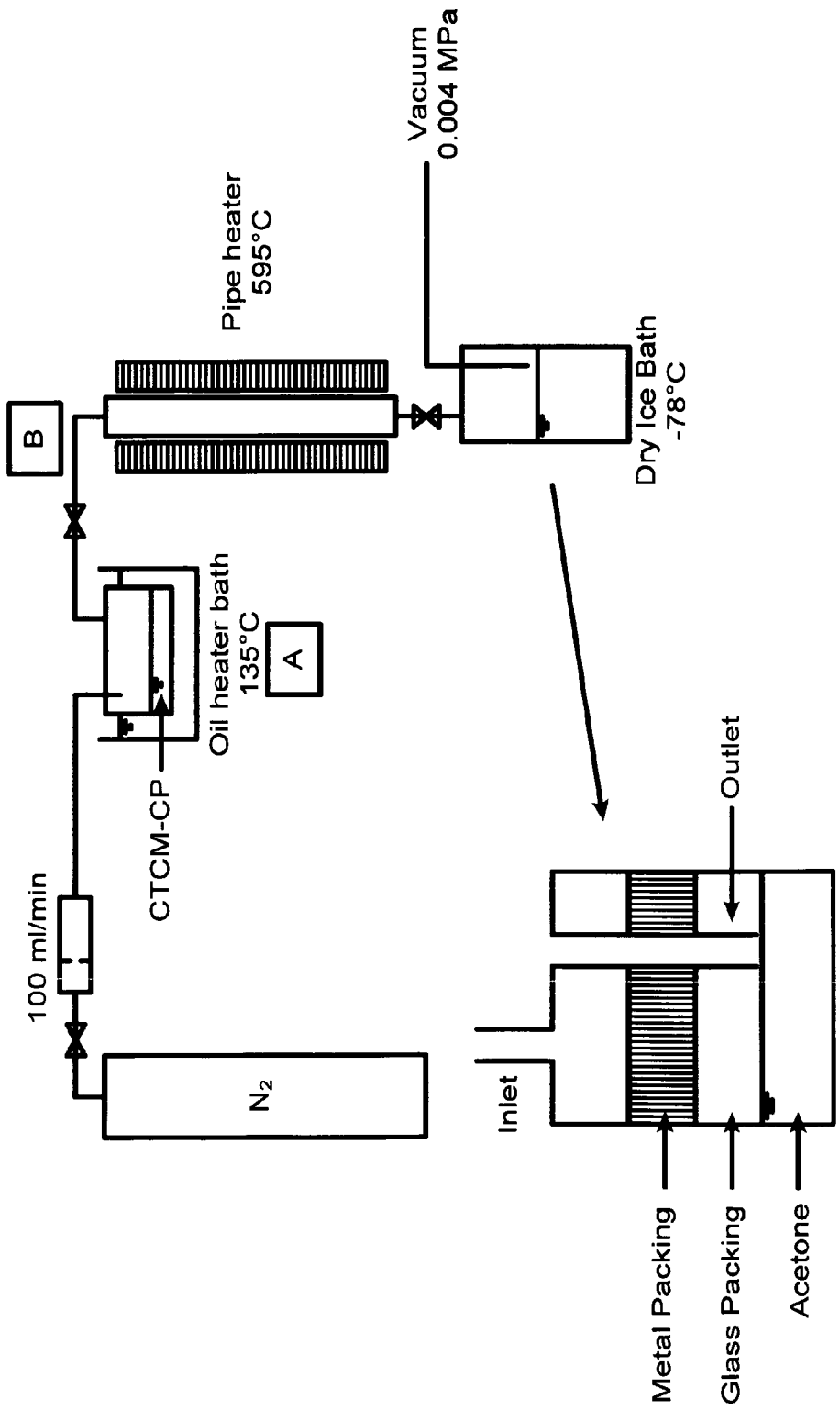
FIG. 1 shows an exemplary rig for preparation of compounds of formula I.

Thus, according to the present invention, there is provided a process for the preparation of the compound of formula I

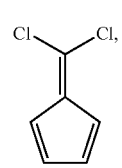
(I)

which process comprises pyrolysing a compound of formula II

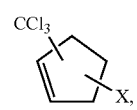
(II)

wherein X is chloro or bromo, preferably chloro at temperatures of at least 200° C.

The pyrolysis temperature should be chosen high enough to allow spontaneous HCl elimination. The pyrolysis reaction preferably takes place in a reactor at temperatures of preferably from 200 to 1000° C., more preferably from 400 to 800° C. An example of suitable reactors for the pyrolysis reaction are tubular reactors (pipe heaters) available from e.g. Parr Instrument Company, 211 Fifty Third Street, Moline, Ill. 61265-9984.

In a preferred embodiment of the invention the compound of formula II is conveyed to the reactor in gaseous form.

In another preferred embodiment a carrier gas can be used for the transport of the gaseous compound of formula II into the reactor. The compound of formula II is then conveyed to the reactor under continuous carrier gas flow. Preferably, gaseous hydrogen chloride, an inert gas like nitrogen or an evaporated solvent like xylene is used as carrier gas. Since gaseous hydrogen chloride is a by-product of the pyrolysis reaction, parts of the reactor exhaust stream can be advantageously used as the carrier gas. Alternatively, the compound of formula II or a solution of it can be directly sprayed into the reactor.

Preferably the product is transferred after the pyrolysis reaction from the outlet of the reactor into a cooled trap. The temperature of trap can vary within wide limits. The trap is preferably kept at a temperature from +150° C. to −150° C., in particular at +70° C. to −70° C., preferably from +30 to −70° C.

The trap can be filled with inert material which is able to increase the surface area of the trap, in particular with a metal and/or glass packing so that the compound of formula I can condense on the surface of the packing. In another embodiment of the invention the compound of formula I is absorbed into a solvent or co-condensed with a solvent. Preferred solvents are acetone, toluene or xylene and mixtures thereof.

It is also advantageous to use the compound in gaseous form directly into the succeeding stage of the synthesis of fungicidally active compounds as described in WO 2007/048556.

The pressure for performing the reaction can vary within wide limits and can be selected depending on the method of feeding the reactor. Pressures under atmospheric pressure are preferred if the compound of formula II is conveyed into the reactor in gaseous form. Reduced pressure gives a lower condensation temperature which is beneficial in avoiding high liquid temperatures when the product is unstable, which is the case here. Higher pressure brings the benefit of reduced reactor volume. The selection of a beneficial pressure is within the skills of an artisan.

In a preferred embodiment of the invention the reactor for the pyrolysis reaction and the vessel which contains the compound of formula II is kept under reduced pressure, in particular under a pressure from 0.008 to 0.08 Mpa, in particular under 0.004 Mpa to 0.04 Mpa.

The pyrolysis of the compound of formula II to the compound of formula I is a two stage reaction in which in situ intermediates of formula IIIe, IIIf and IIIg are formed which then react to the compound of formula I (X is chloro or bromo):

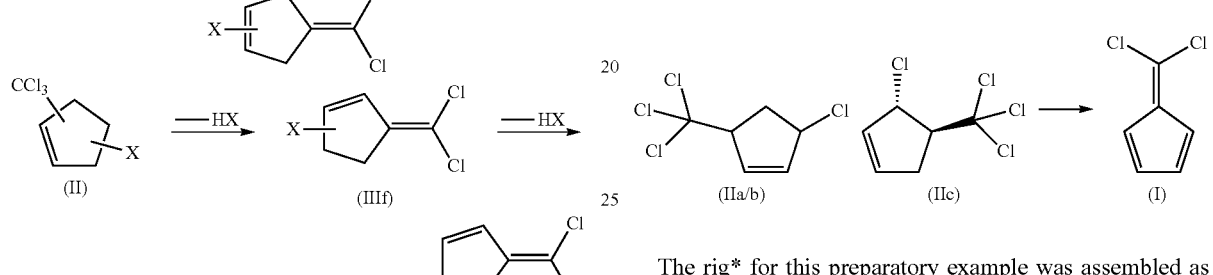

The intermediates of formulae IIIe and IIIf wherein X is chloro or bromo, are novel and form further aspects of the invention. Depending on the isomer content of the compound of formula II, the compounds of formulae IIIe, IIIf and IIIg can occur in different isomeric forms, here shown for the compounds of formula III, wherein X is chloro:

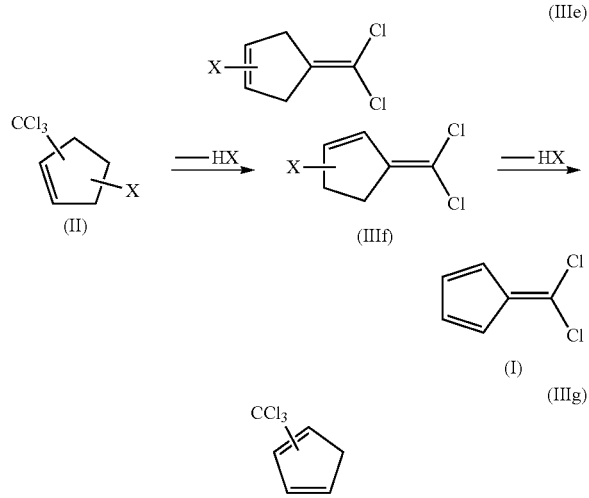

Alternatively, the compound of formula III can also be prepared for example by contacting aqueous sodium hydroxide with an organic solution of the compound of formula II. Since the intermediate of formula III is a chemically stable compound, the compound of formula I can also be prepared by pyrolysing a compound of formula III (IIIe, IIIf and IIIg) which itself has been prepared by a process other than pyrolysis. This process variant also forms a further aspect of this invention. The reaction conditions including the preferred embodiments and temperature ranges are the same as mentioned above for the pyrolysis of the compound of formula II to the compound of formula I.

PREPARATORY EXAMPLES

Example P1

Preparation of the Compound of Formula I, Variant with Carrier Gas

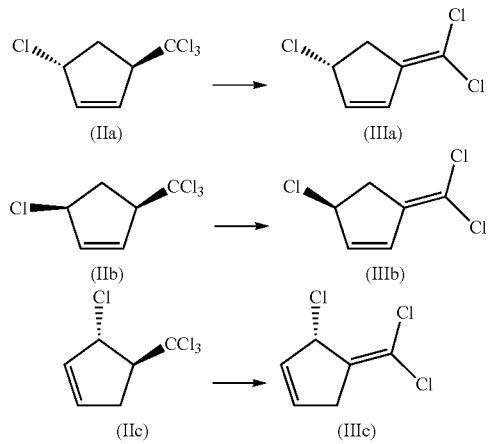

The rig* for this preparatory example was assembled as shown in FIG. 1. A 500 ml Parr reactor was used as the trapping vessel and was pre-packed with glass and metal packing material (2:1 ratio) in order to maximise the trapping surface area. Approximately 50 ml of acetone was also charged into the trap, ensuring the level was kept below that of the outlet pipe (see expansion in FIG. 1). The trap was submerged in a dry ice/acetone bath and given time to equilibrate at approximately −70° C. The pipe heater was pre-heated to 595° C. and the entry pipe (B) was preheated to 250° C. through use of an electric rope heater. The compound of formula II (15 g, a mixture of isomers IIa, IIb and IIc in a ratio of 66:8:26) was charged to a 25 ml 3-necked round-bottomed flask (A)—One neck was connected to the entry pipe to the furnace, the second served as an inlet for the nitrogen flow and the final neck was equipped with a vacuum monitor. The vessel containing the compound of formula IId (containing all isomeric forms) was heated to 135° C. with a nitrogen flow rate of approximately 100 ml/min. A vacuum of 0.004 Mpa was then applied and the process was allowed to proceed for 90-120 minutes. Upon completion, as adjudged by observing the loss of compound of formula IId, the trap was disconnected. All connections and components of the trap were rinsed with acetone and the resulting deep orange solution was filtered. Analysis by GC through use of an internal standard revealed a collected yields of 87% (8.7 g) compound of formula I and only very minor traces of compound of formula IId.

* materials of construction throughout rig: glass and stainless steel.

Example P2

Preparation of the Compound of Formula I, Variant without Carrier Gas

Repeating the experiment of example P1 without the nitrogen flow resulted in a collected yield of 80% (8.0 g) of compound of formula I.

Example P3

Figure 2:
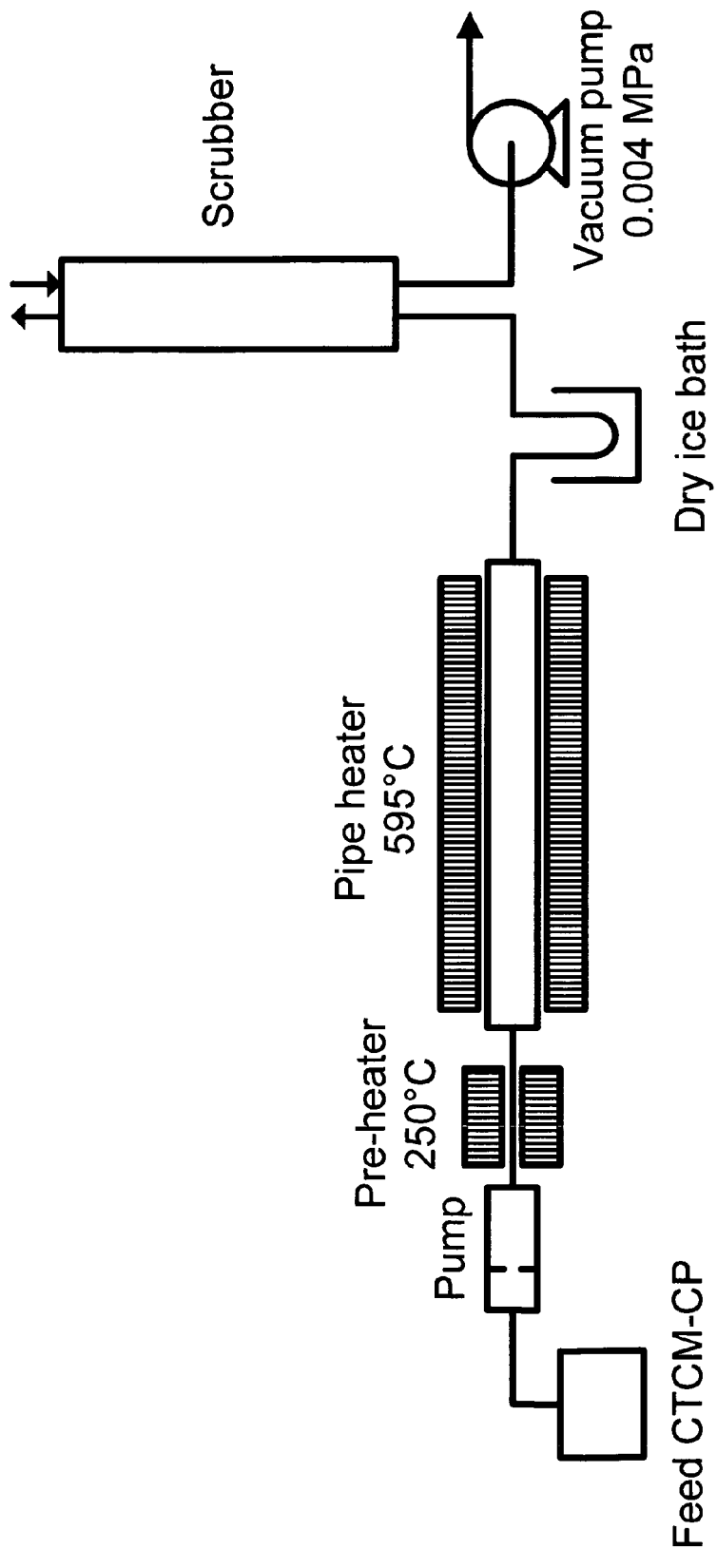
FIG. 2 shows another exemplary rig for preparation of compounds of formula I.

Preparation of the Compound of Formula I, Variant with Continuous Liquid Feed into the Pre-Heater The compound of formula IIa (21 g) was delivered to the preheated chamber via a pump at a flow rate of approximately 0.2 ml/min as shown in FIG. 2. A vacuum of 0.004 Mpa was then applied and the process was allowed to proceed for 90-120 minutes. Upon completion, the product treated was analysed as for Example P1. Analysis by GC through use of an internal standard revealed collected yields of up to 72% (13.9 g) compound of formula I and 8% recovery (2.1 g) of compound of formula IId.

Example P4

Preparation of Compounds of Formula IIIa and IIIb

Figure 3:
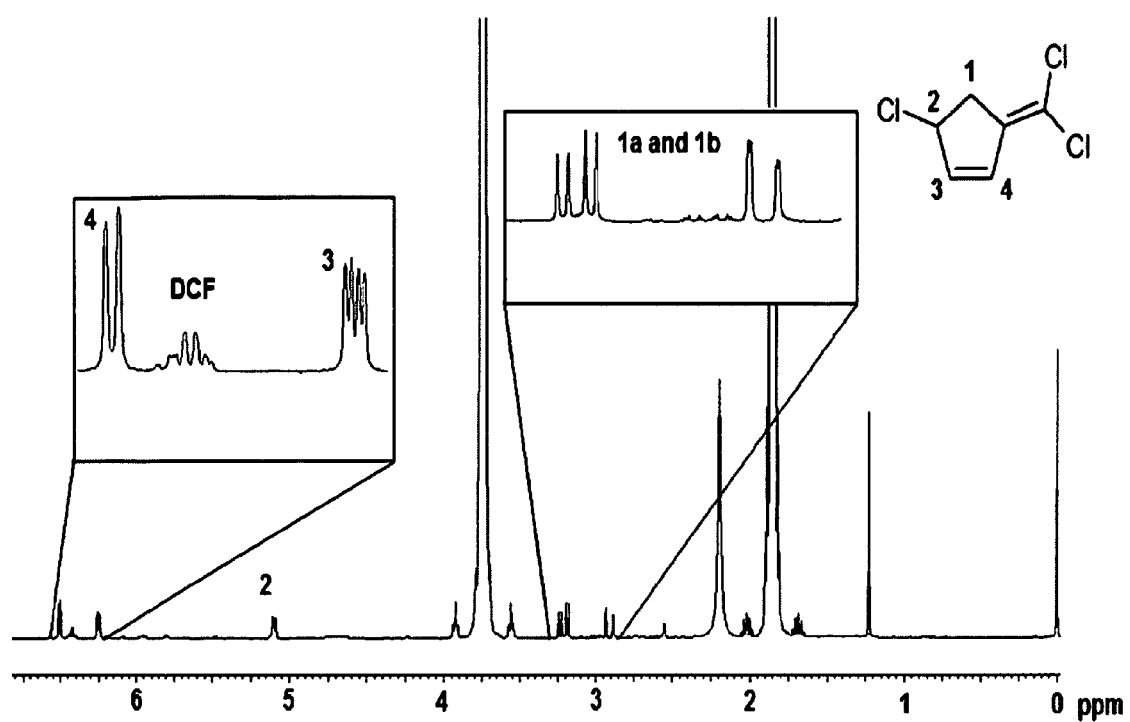
FIG. 3 shows an NMR for compounds of formula IIIa and IIIb.

A solution of isomers of formulae IIa, IIb and IIc (22 g in a ratio of 66:8:26) in toluene (266 ml) was added to a mixture of 25% NaOH (aq, 133 ml), benzyltriethylammonium chloride (5.67 g, 25 mol%) and pinacol (3 g, 25 mol%) and stirred at 40° C. After 30 minutes, as adjudged by GC analysis, the chemical yield of the compounds of formulae IIIa and IIIb versus an internal standard was approximately 90%. At this stage, water (200 ml) was added and the organic layer was separated and dried over magnesium sulfate. Filtration, followed by concentration under vacuum afforded the compounds of formulae IIIa and IIIb as a brown oil (70%, 12.8 g). The NMR is depicted as FIG. 3. (DCF signifies dichlorofulvene.)

What is claimed is:

1. A process for the preparation of the compound of formula I

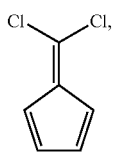
(I)

which process comprises pyrolysing a compound of formula II

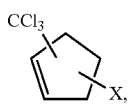
(II)

wherein X is chloro or bromo at temperatures of at least 200° C.

2. A process according to claim 1, wherein the compound of formula II is pyrolysed in a reactor at temperatures of 200 to 1000° C.

3. A process according to claim 2, wherein the compound of formula II is conveyed to the reactor in gaseous form.

4. A process according to claim 3, wherein the compound of formula II is conveyed to the reactor under continuous carrier gas flow.

5. A process according to claim 4, wherein the carrier gas is selected from nitrogen, gaseous hydrogen chloride and gaseous xylene.

6. A process according to claim 2, wherein the product is transferred after the pyrolysis reaction from the outlet of the reactor into a trap containing an inert solvent.

7. A process according to claim 2, wherein the reactor and the vessel containing the compound of formula II is kept under reduced pressure.

8. A process according to claim 1, wherein X is chloro.

9. A compound of formula IIIe

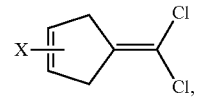
(IIIe)

wherein X is chloro or bromo.

10. A compound of formula IIIf

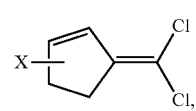
(IIIf)

wherein X is chloro or bromo.

11. A process for the preparation of the compound of formula I which process comprises pyrolysing a compound of formula IIIe according to claim 9

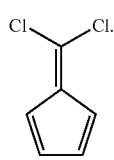
(I)

12. A process for the preparation of the compound of formula I which process comprises pyrolysing a compound of formula IIIf according to claim 10

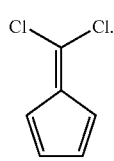
(I)

13. A process for the preparation of the compound of formula I which process comprises pyrolysing a compound of formula IIIg

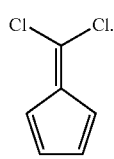
(I)

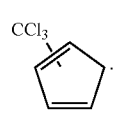
(IIIg)

* * * * *